(12) United States Patent
Amano

(10) Patent No.: US 8,344,326 B2
(45) Date of Patent: Jan. 1, 2013

(54) PET SYSTEM

(75) Inventor: Masaharu Amano, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 13 days.

(21) Appl. No.: 13/057,352

(22) PCT Filed: Aug. 5, 2008

(86) PCT No.: PCT/JP2008/064019
§ 371 (c)(1),
(2), (4) Date: Apr. 14, 2011

(87) PCT Pub. No.: WO2010/016107
PCT Pub. Date: Feb. 11, 2010

(65) Prior Publication Data
US 2011/0198506 A1    Aug. 18, 2011

(51) Int. Cl.
*G01T 1/164* (2006.01)
(52) U.S. Cl. .................................. 250/363.03
(58) Field of Classification Search ........... 250/363, 250/363.01–363.1
See application file for complete search history.

(56) References Cited

U.S. PATENT DOCUMENTS

| | | | |
|---|---|---|---|
| 6,229,870 B1* | 5/2001 | Morgan | 378/9 |
| 2005/0109943 A1* | 5/2005 | Vaquero et al. | 250/363.04 |
| 2006/0124855 A1 | 6/2006 | Gagnon | |
| 2007/0064865 A1* | 3/2007 | Inoue et al. | 378/84 |

FOREIGN PATENT DOCUMENTS

| | | |
|---|---|---|
| JP | 2-48888 U | 4/1990 |
| JP | 2005-98708 A | 4/2005 |
| JP | 2005-312930 A | 11/2005 |
| JP | 2007-93497 A | 4/2007 |
| JP | 2008-134205 A | 6/2008 |

OTHER PUBLICATIONS

PCT International Preliminary Report on Patentability issued on Mar. 8, 2011 for PCT/JP2008/064019.

* cited by examiner

*Primary Examiner* — Kiho Kim
(74) *Attorney, Agent, or Firm* — McDermott Will & Emery LLP

(57) ABSTRACT

A PET instrument free from problems of maintenance of a detector when a field of view in a body axial direction of a subject is significantly enlarged. A gantry (1) is divided into a plurality of units (5) in the body axial direction of the subject. Each unit (5) is configured to be movable in an orthogonal direction to the body axial direction. Further, a number of detectors are provided in each unit (5) and arranged in its circumferential direction and the body axial direction.

6 Claims, 3 Drawing Sheets

A

B

C

PET SYSTEM

CROSS REFERENCE TO RELATED APPLICATIONS

This application is a National Stage application under 35 U.S.C. §371, of International Application No. PCT/JP2008/064019 filed on Aug. 5, 2008, which was published as WO 2010/016107 on Feb. 11, 2010. The application is incorporated herein by reference.

TECHNICAL FIELD

This invention relates to a PET system.

BACKGROUND

A PET (Positron Emission Tomography) system is employed as a medical imaging and diagnosis device (for example, see Japanese Laid-Open Patent Publication No, 2005-312930). The PET system is a device for making a picture of a body distribution of a positron labeling agent injected into the human body. As shown in FIG. 5, it is well known that a tunnel 2 is formed in a gantry 1 and a subject is laid on a top board 4 of an examining table 3, and the top board 4 with the subject is inserted into the tunnel 2. A number of detectors are incorporated in the gantry 1 for detecting radioactive rays.

For improvement of the PET systems, the field of view in a direction of the body axis of the subject has been discussed. Currently, each detector is arranged in a region whose length is limited in a direction of the body axis of the subject, and thereby, the field of view is as small as about 15 cm to 25 cm long. However, it is certain that the field of view in the direction of the body axis will be largely increased in the future by significantly enlarging the gantry 1 and incorporating detectors in the gantry 1 over its entire length in the future. It is anticipated, for example, that the view field in the direction of the body axis will be increased to a length of about 100 cm so as to simultaneously diagnose the entire torso of the subject. It is also foreseeable that the view field in the direction of the body axis will be increased to a length of about 180 cm so as to simultaneously diagnose the whole body from the top of the head to the toes of the subject.

In such cases, however, there will be a problem that maintenance becomes difficult because an operator cannot easily access detectors located at the middle of the gantry in the direction of the body axis, for example, in order to change the detectors.

Accordingly, an object of the present invention is to eliminate the problem of the detector's maintenance in a PET system, when the field of view in the direction of the body axis of the PET system is significantly enlarged.

SUMMARY OF THE INVENTION

This invention provides a gantry having a novel structure. The gantry is cylindrical and extends along the body axis of a subject. The gantry is divided into more than three units in a direction of the body axis and each of the second and later units is movable in a direction perpendicular to the body axis. A large number of detectors are incorporated in each of the units in such a way that the detectors are aligned in directions of a circumference of the unit and the body axis.

According to an example, a plurality of boxes are arranged in each of the units for receiving the detectors. Each of the boxes has a length corresponding to a length of the unit and extends along the body axis in such a way that both ends of the box match with both ends of the unit. The boxes are aligned in the direction of the circumference of the unit. A support means is arranged in each of the units for supporting the respective boxes at an outer circumference of the boxes.

In addition, the support means comprises a ring and the ring is arranged around the aligned boxes, and the ring supports the respective boxes at the outer circumference of the boxes.

DETAILED DESCRIPTION OF THE INVENTION

Figure 1:
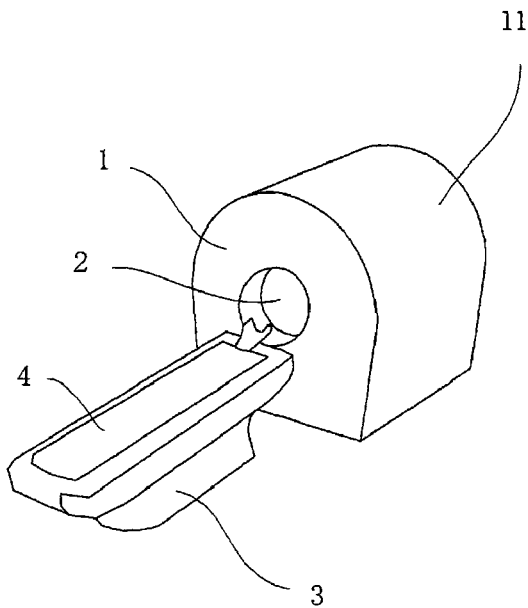
FIG. 1 is a perspective view showing an embodiment of the present invention.
Figure 5:
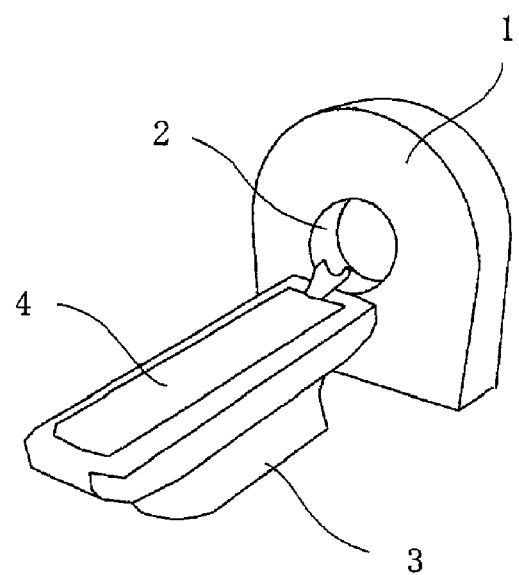
FIG. 5 is a perspective view of a conventional PET system.

FIG. 1 shows a PET system according to an example of the present invention. In this PET system, similarly to the conventional PET system shown in FIG. 5, a tunnel 2 is formed in a gantry 1, a subject is laid on a top board 4 of an examining table 3, and the top board 4 with the subject is inserted into the tunnel 2. However, the gantry 1 has a novel structure. The structure is as follows.

Figure 2:
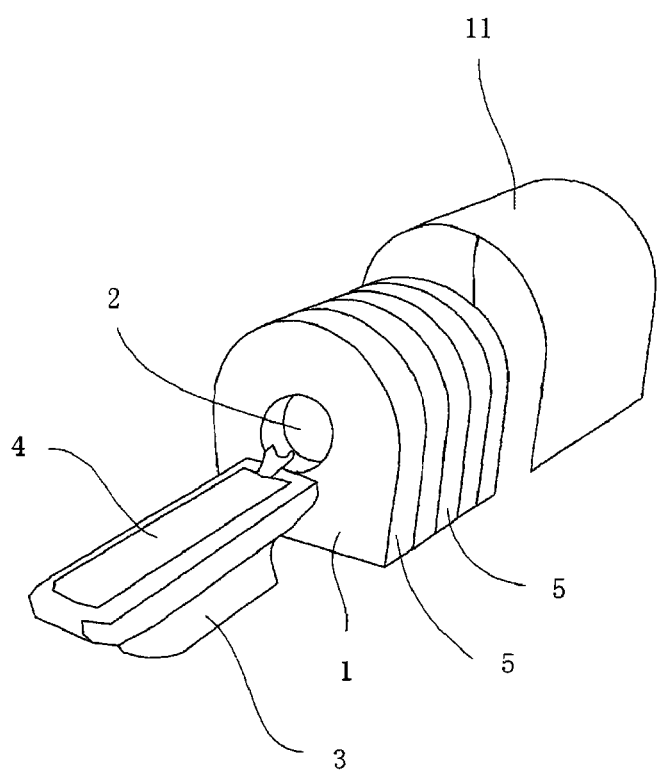
FIG. 2 is a perspective view similar to FIG. 1, wherein the cover is moved.
Figure 3:
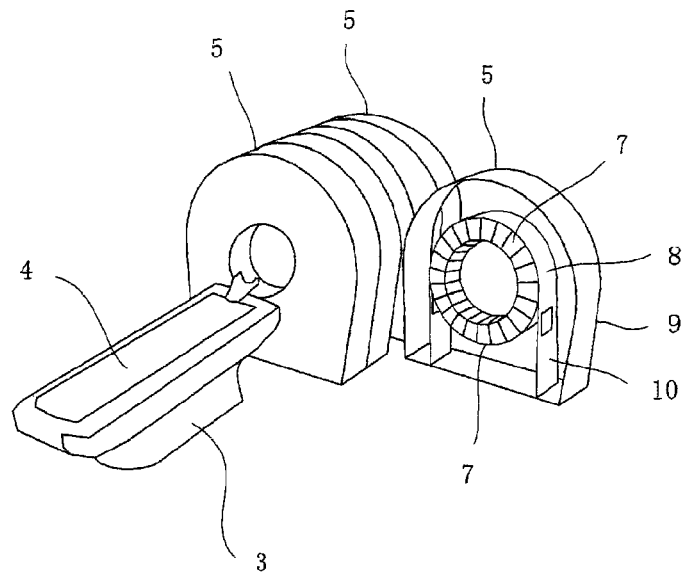
FIG. 3 is a perspective view similar to FIG. 2, wherein the unit is moved.

In this PET system, the gantry 1 is largely extended in a direction of the body axis of the subject. The gantry 1 is cylindrical and extends along body axis. As shown in FIG. 2 and FIG. 3, the gantry 1 is divided into a plurality of units 5 in the direction of the body axis. Each of the units 5 is movable in a direction perpendicular to the body axis. For example, a guide is arranged below the gantry 1 and each of the units 5 is supported and guided by the guide. Each of the units 5 can be slid along the guide and thus moved in directions horizontal and vertical to the body axis. The unit 5 may be moved by a driving mechanism.

Figure 4:
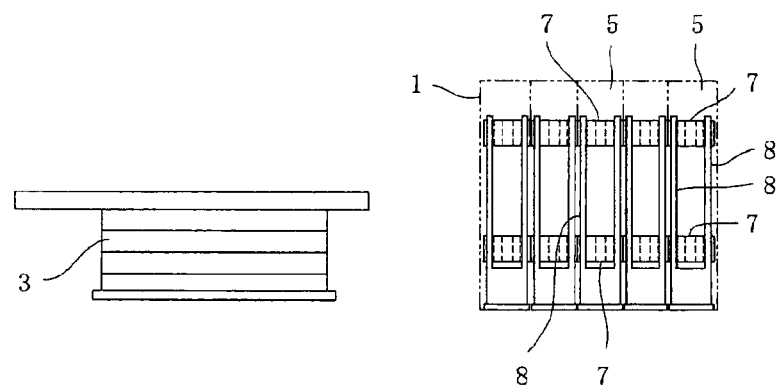
FIG. 4A is an illustration diagram of the PET system shown in FIG. 1.
FIG. 4B is a perspective view of the box shown in FIG. 4A.
FIG. 4C is a perspective view of the detectors shown in FIG. 4A.
Figure 4:
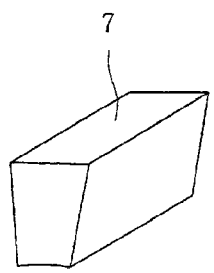
Figure 4:
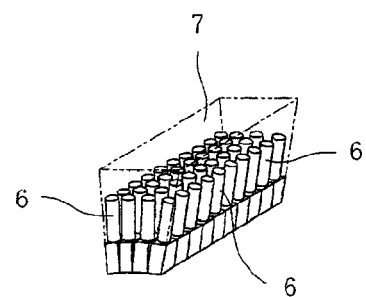

As shown in FIG. 4, a large number of detectors 6 are incorporated in each of the units 5 in such a way that the detectors 6 are aligned in directions of a circumference of the unit 5 and the body axis. The detectors 6 are connected between the units through cables. According to this embodiment, a plurality of boxes 7 are arranged in each of the units 5 for receiving the detectors 6. Each of the boxes 7 has a length corresponding to a length of the unit 5 and extends along the body axis in such a way that both ends of the box 7 matches with both ends of the unit 5. The boxes 7 are aligned in the direction of the circumference of the unit 5. A support means is arranged in each of the units 5 for supporting the respective boxes 7 at an outer circumference of the boxes 7.

In addition, according to this example, the support means comprises a ring 8. The ring 8 is arranged around the aligned boxes 7 so as to hold the respective boxes 7. The unit 5 further comprises a horseshoe-shaped frame 9. The boxes 7 and the ring 8 are arranged inside the frame 9, the ring 8 is provided with legs 10, and the legs 10 are secured to the frame 9 of the unit 5. Thus the respective boxes 7 are supported at their outer circumference by the ring 8 and the legs 10. The ring 8 is formed by bending a thin plastic or metal sheet into a curve. The ring 8 may be circular, or polygonal. A width of the ring corresponds to the length of the boxes 7. The legs 10 are also made of a thin plastic or metal sheet and formed integrally with the ring 8.

Each of the units 5 is covered with a cover 11.

Thus, in this PET system, the gantry 1 is largely extended along the body axis, and the detectors 6 are provided over the entire length of the gantry. Accordingly the field of view in the direction of the body axis is largely increased. For example, the view field in the direction of the body axis is increased up to a length of about 100 cm, and thereby, the entire torso of the subject is diagnosed simultaneously. It is also possible that the view field in the direction of the body axis is increased up to a length of about 180 cm, and thereby, the whole body from the top of the head to the toes of the subject is diagnosed simultaneously.

Furthermore, for example, when the detectors 6 are changed, the cover 11 is first moved along the units 5 to expose the units 5. After that, a specific unit 6 of the units 5 is moved in a direction perpendicular to the body axis until its boxes 7 are exposed. Thus, even though the gantry 1 is largely extended along the body axis, the operator can easily access the detectors 6 located at the middle of the gantry 1 in the direction of the body axis and the detector's maintenance is facilitated.

In this PET system, the boxes 7 are supported at their outer circumference as described above. Therefore, the respective boxes 7 need not be supported at their end faces, that is, by the support means arranged between the units 5 and opposite to the end faces of the boxes 7. As a result, the boxes 7 can be positioned in contact with or in closely to each other between the units 5 without any gaps. Consequently, loss of data detected by the detectors 6 are not caused, which prevents the sensitivity of the PET system from being reduced.

In addition, the ring 8 is arranged around the aligned boxes 7 and the boxes 7 are supported by the ring 8 at their outer circumference, as described above. Consequently, the boxes 7 can be held and supported by the ring 8 easily and appropriately.

The invention claimed is:

1. A PET system, comprising:
  a cylindrical gantry extending along the body axis of a subject and divided into three or more units in a direction of said body axis, each of the second and later units being movable in a direction perpendicular to said body axis; and
  a number of detectors incorporated in each of said units in such a way that said detectors are aligned in directions of a circumference of said unit and said body axis.

2. The PET system according to claim 1, further comprising:
  a plurality of boxes arranged in each of said units for receiving said detectors, each of said boxes having a length corresponding to a length of said unit and extending along said body axis in such a way that both ends of said boxes are flush with both ends of said unit, said boxes being aligned in the direction of the circumference of said unit; and
  a support arranged in said each of said units for supporting said boxes at an outer circumference of said boxes,
  wherein the boxes of one of units are positioned in substantially contact with the boxes of adjacent one of units.

3. The PET system according to claim 2, wherein said support comprises a ring and said ring is arranged around the aligned boxes, and said ring supports said respective boxes at the outer circumference of said boxes.

4. The PET system according to claim 2, wherein the view field in the direction of the body axis is 100 cm or more.

5. The PET system according to claim 1, wherein an outer shape of the units is a horseshoe-shape.

6. The PET system according to claim 1, further comprising a cover covering the units.

* * * * *